United States Patent
Yang et al.

(10) Patent No.: US 7,923,486 B2
(45) Date of Patent: Apr. 12, 2011

(54) BIO-POLYMER AND SCAFFOLD-SHEET METHOD FOR TISSUE ENGINEERING

(75) Inventors: Jian Yang, Arlington, TX (US);
Jagannath Dey, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 447 days.

(21) Appl. No.: 11/906,962

(22) Filed: Oct. 4, 2007

(65) Prior Publication Data

US 2009/0093565 A1 Apr. 9, 2009

(51) Int. Cl.
*A61F 2/00* (2006.01)
*A61L 24/00* (2006.01)
(52) U.S. Cl. ........................................................ 523/113
(58) Field of Classification Search .................. 523/113; 532/113
See application file for complete search history.

(56) References Cited

U.S. PATENT DOCUMENTS

| | | | | | |
|---|---|---|---|---|---|
| 4,837,115 | A | * | 6/1989 | Igarashi et al. | 428/36.92 |
| 5,665,831 | A | * | 9/1997 | Neuenschwander et al. | 525/415 |
| 5,776,989 | A | * | 7/1998 | Kubota et al. | 521/48 |
| 5,993,843 | A | * | 11/1999 | Sakurada et al. | 424/409 |
| 6,005,066 | A | * | 12/1999 | Lehrle et al. | 528/328 |
| 6,228,969 | B1 | * | 5/2001 | Lee et al. | 528/80 |
| 7,037,984 | B2 | * | 5/2006 | Lendlein et al. | 525/454 |
| 7,173,102 | B2 | * | 2/2007 | DeGrado et al. | 528/322 |
| 7,186,789 | B2 | * | 3/2007 | Hossainy et al. | 528/272 |
| 2002/0142413 | A1 | * | 10/2002 | Brady et al. | 435/181 |
| 2005/0053840 | A1 | * | 3/2005 | Jo et al. | 429/247 |
| 2005/0063939 | A1 | * | 3/2005 | Ameer et al. | 424/78.37 |
| 2005/0090607 | A1 | * | 4/2005 | Tapsak et al. | 524/588 |
| 2005/0106120 | A1 | * | 5/2005 | Cheng et al. | 424/78.27 |
| 2005/0238683 | A1 | * | 10/2005 | Adhikari et al. | 424/423 |
| 2006/0014842 | A1 | * | 1/2006 | Li et al. | 521/61 |
| 2006/0177416 | A1 | * | 8/2006 | Turnell et al. | 424/78.27 |
| 2007/0003594 | A1 | * | 1/2007 | Brady et al. | 424/426 |
| 2007/0015894 | A1 | * | 1/2007 | Heijkants et al. | 528/44 |

(Continued)

OTHER PUBLICATIONS

Jian Yang, Antonio R. Webb, Samuel J. Pickerill, Gretchen Hageman, Guillermo Ameer "Synthesis and evaluation of poly(diol citrate) biodegradable elastomers" Nov. 15, 2005, www.sciencedirect.com Biomaterilas 27(2006) 1889-1898.*

*Primary Examiner* — Mark Eashoo
*Assistant Examiner* — Angela C Scott
(74) *Attorney, Agent, or Firm* — Edwin S. Flores; Chalker Flores, LLP (57) ABSTRACT

A method of making a new type of biomaterials, biodegrable crosslinked urethane-containing polyester (CUPE) elastomers and a scaffold-sheet engineering method for tissue engineering applications is provided. CUPEs can be synthesized by forming a linear pre-polymer, which is a polyester, introducing the urethane bonds into polyester using a diisocyanate as a linker, and crosslinking the resulting urethane containing linear polymers to form CUPEs via post-polymerization. This family of polymers, CUPEs, exhibit excellent biocompatibility with desired degradation. Tissue engineering scaffolds made of CUPEs are soft and elastic, and have good mechanical strength. Complex tissue grafts can be constructed by a novel layer-by-layer (LBL) scaffold-sheet engineering design using CUPE sheets. CUPE scaffolds can provide openings for cell to cell communication across scaffold layers and angiogenesis into the depth of the construct. Biomolecules, such as anticoagulants, can be incorporated into the CUPE polymers, increasing their viability as vascular graft scaffolds.

19 Claims, 10 Drawing Sheets

U.S. PATENT DOCUMENTS

| | | | |
|---|---|---|---|
| 2007/0037954 A1* | 2/2007 | Heijkants et al. | 528/44 |
| 2007/0043033 A1* | 2/2007 | Glick et al. | 514/221 |
| 2007/0134332 A1* | 6/2007 | Turnell et al. | 424/486 |
| 2007/0248567 A1* | 10/2007 | Pathak et al. | 424/78.27 |
| 2008/0262613 A1* | 10/2008 | Gogolewski | 623/11.11 |

* cited by examiner

BIO-POLYMER AND SCAFFOLD-SHEET METHOD FOR TISSUE ENGINEERING

BACKGROUND OF THE INVENTION

The present invention addresses the shortage of suitable biomaterials and scaffolds for soft tissue engineering. A specific example of the present invention relates to tissue engineering of small diameter blood vessels (SDBV).

Tissue engineering, or regenerating fully functional and viable tissue grafts, is conventionally limited to tissue thickness less than 1 mm thick. Regenerating vascularized tissue remains elusive as well. Tissue engineering faces many challenges, most of them related to biocompatibility. Biocompatibility comprises factors such as material, chemical, and mechanical compatibility with the host. Limitations in cell sources, cell availability, also compounds the challenges of tissue engineering. Since the National Science Foundation coined the term "tissue engineering" in 1987, creating suitable biomaterials and appropriate scaffold engineering designs have been an ongoing endeavor.

The common tissue engineering model is to seed cells, autologous adult cells, stem cells, or progenitor cells into biodegradable scaffolds. The biodegradable scaffold acts as a temporary template for diseased tissues. The cell-seeded construct is then implanted to the target site in the body for tissue regeneration. The plan is that cells produce their own matrix, and new tissues form while the scaffold is gradually absorbed.

Biodegradable polymers with elastomeric properties have recently received attention for their potential use in the engineering of soft tissues such as blood vessel, heart valves, cartilage, tendon, and bladder, which exhibit elastic properties.

Vascular disease and the need for a suitable replacement of diseased tissue remains a challenge, with atherosclerotic vascular disease being the leading cause of mortality in the United States. (A report from the American Heart Association statistics committee and stroke statistics subcommittee. Heart Disease and Stroke Statistics—2006 update, 2006) . Coronary artery and peripheral vascular, SDBVs, of less than 6 mm diameter, frequently require bypass grafts. Autogenous veins, expanded polytetrafluoro-ethylene (ePTFE), and Dacron bypass grafts have been used for replacing diseased blood vessels. However, a large number of bypass grafts fail postoperatively. Acute thrombosis occurs in the early postoperative period or intimal hyperplasia (IH) occurs within months or years. Hence, multiple surgical or coronary angioplasty procedures are often required.

Tissue engineering may be able to provide a biocompatible graft with long term patency. However, tissue engineered SDBV have not attained long term patency to date.

The challenges to SDBV tissue engineering and corresponding biocompatibility are many. A suitable biomaterial needs to perform mechanical graft functions such as support for the vascular cells, a temporary extra-cellular matrix. The desired biomaterial performs analogous to a native blood vessel, having suitable strength, elasticity, and compliance. The scaffold should permit even cell distribution and nutrient delivery at matrix depths greater than 300 μm.

Compliance mismatch and or lack of strength can lead to thrombosis and/or significant inflammatory responses. Early efforts on vascular tissue engineering focused on using biodegradable synthetic polymer, such as polylactide (PLA), polyglycolide (PGA), and polycaprolactone (PCL) and their copolymers. These polymers were rolled into tubes and implanted in vivo but did not yield favorable results due to mismatch in mechanical properties and inflammatory responses.

Natural polymers, such as collagen, hyaluronic acid, chitosan, and fibrin often lack the strength and elasticity needed for vascular graft materials. (Neider et al., Biomaterials, 2002, 23(17): p. 3717-3731; Boccafoschi et al., Biomaterials, 2005, 26(35): p. 7410-7417; Remuzzi et al., Tissue Eng., 2004. 10(5-6): p. 699-710; 37. Zhang et al., J Biomed Mater Res A, 2006, 77A(2): p. 277-284). Studies using natural polymers have been unsuccessful and none of the tubes made from the natural materials above can fully represent the anatomical structure of blood vessels. Some studies have explored the use of two dimensional cell sheets to regenerate tissue, for example, SDBV. However, these tissue constructs require months of in vitro maturation and one study failed to maintain patency in vivo for more than 7 days. (L'Heureux et al., Faseb J, 1998. 12(1): p. 47-56.)

Polyurethanes are a family of polymers which have the requisite strength, elasticity and other mechanical properties to serve as functional vascular grafts. However, some of the limiting factors for urethanes is their tendency to produce creep under cyclic deformation, their poor cell compatibility and their long degradation times.

Crosslinked polyesters, like polydiol citrates have been shown to demonstrate good tolerance to creep, excellent cell compatibility and hemocompatibility and controllable degradation times. However, polydiol citrates don't have the necessary elasticity and strength to be suturable, which is one of the primary requirements of a vascular graft material Good scaffold candidates for engineering SDBV would have good biocompatibility, which includes hemocompatibility and biodegradability. Potential scaffolds would be cell, tissue, and blood compatible. Vascular cells seeded in the scaffold would yield collagen and elastin in quantities similar to those of the native vessels. Ideal scaffolds should be non-thrombogenic and conducive to continuous endothelium layer formation. The degradation rate of the scaffolds should approach the tissue growth or remodeling rate.

It is desirable for a scaffold to have architecture which is similar to the native blood vessel. The scaffolds should compartmentalize and support fibroblasts, smooth muscle cells (SMCs), and endothelial cells (ECs). Cells should adhere to the scaffold, grow, and differentiate. The scaffold should afford communication of the cells within and across cell types.

Scaffolds should provide mechanical biocompatibility, soft and elastic, similar to the native blood vessel. Elasticity is desired to avoid compliance mismatch which was believed to contribute intimal hyperplasia, a major reason for graft failure. (Teebken et al., Eur. J. Vasc. Endovasc., 2002. 23(6): p. 475-48518; 58. He et al., Tissue Eng, 2002. 8(2): p. 213-224; Lemson et al., Eur. J. Vasc. Endovasc., 2000. 19(4): p. 336-350.) They should be able to withstand cyclic deformation without irritation to the surrounding tissues. (Wang et al., Nat. Biotechnol., 2002. 20(6): p. 602-606.)

Even when scaffolds are used for other soft tissue generation, they should permit rapid angiogenesis provide a blood supply by which nutrients are supplied to the repair site and through which waste is removed, it also provides direct access of the graft to the host's immune system to limit infection. (Hodde J., Tissue Eng, 2002. 8(2): p. 295-308.) Soft scaffolds should promote scaffold-tissue adaptation without significant mechanical irritation to the hosting tissues. Soft scaffolds should also facilitate scaffold-assembling into various shapes through, for example, folding, rolling trimming, and bending.

For in vivo tissue engineering, the scaffolds should be functional for immediate implantation.

More recently, the use of soft and elastic biodegradable crosslinked poly(diol citrates) elastomers with a biphasic scaffold design showed promise for SDBV applications. However, the low molecular weight of these polymers raises processing concerns. And further, the outermost adventia layer is absent these SDBVs and suturability of the scaffold is lacking. (Yang et al., Tissue Engr., 2005, 11(11-12): p 1876-1886). Linear polyurethanes possess strong mechanical properties depending on the composition of their hard and soft segment. However, the degradability, biocompatibility, and susceptibility to permanent creep of polyurethanes still challenge their use for vascular regeneration.

Promising scaffold candidate material will be somewhat porous. It has been shown that ECs and SMCs can influence each other via heterocellular junctions and the signaling molecules secreted by both cell types. In turn, porosity which allows transfer of bio-macromolecules is desirable.

SUMMARY OF THE INVENTION

The present invention addresses the shortage of suitable biomaterials and scaffolds for soft tissue engineering. In particular, tissue-engineered SDBVs benefit from the present invention. A novel family of biodegradable elastomers, Crosslinked Urethane-containing Polyester (CUPE) is developed and employed in engineering SDBV via a scaffold-sheet design.

One aspect of the present invention is to use a porogen to obtain surface roughness and scaffold openings or tunnels. In an exemplary embodiment, poly(ethylene glycol) dimethyl ether (PEGDM) is used as a porogen mixed with pre-poly 1,8-octanediol citrate (POC) polymer solution. After solvent evaporation and post-polymerization, the PEGDM was leached out to obtain a POC' film featured with a couple of sub-micron (nano) of surface roughness and tortuous tunnels inside which are similar in dimension to the fenestrations of elastic lamina.

Another aspect of the present invention is to permit bovine serum albumin (BSA) to penetrate into tortuous POC' film. In contrast to regular POC, in which BSA only adsorbed on the surface.

Another aspect of the POC' is that it is cohesive but not sticky. Further this nano-featured membrane can physically bond to itself. That is one POC' membrane can bond to another POC' membrane.

Another aspect of the present invention is to facilitate compartmentalization of cell types. For example in SDBV, the present invention enables compartmentalization of the three types of cells (fibroblasts, SMCs and ECs) without hampering the cell-cell communication between SMCs and ECs.

Another aspect of the present invention is to promote even cell distribution across a scaffold.

Another aspect of the present invention is to provide compliance matching with native tissue.

Another aspect of the present invention is to provide off-the-shelf availability for in vivo tissue-engineering of SDBV.

Other aspects of the present invention include adequate strength, creep-resistance, and suture-ability.

Other aspects of the present invention include providing biocompatibility through rate of degradation commensurate with tissue regeneration.

BRIEF DESCRIPTION OF THE FIGURES

For more complete understanding of the features and advantages of the present invention, reference is now made to the detailed description of the invention along with the accompanying figures, wherein.

DETAILED DESCRIPTION OF THE INVENTION

The invention, as defined by the claims, may be better understood by reference to the following detailed description. The description is meant to be read with reference to the figures contained herein. This detailed description relates to examples of the claimed subject matter for illustrative purposes, and is in no way meant to limit the scope of the invention. The specific aspects and embodiments discussed herein are merely illustrative of ways to make and use the invention, and do not limit the scope of the invention.

Figure 1A:
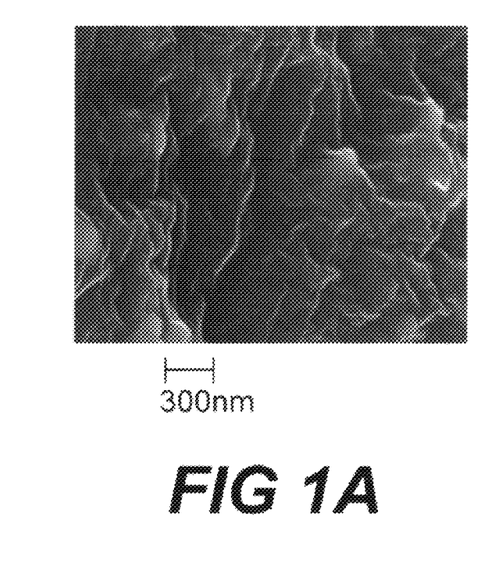
FIGS. 1A-1B are photographs of scanning electron microscopy (SEM) images of a POC membrane, according to an exemplary embodiment of the present invention, where A) shows surface morphology and B) shows a cross-section of the membrane.
Figure 1B:
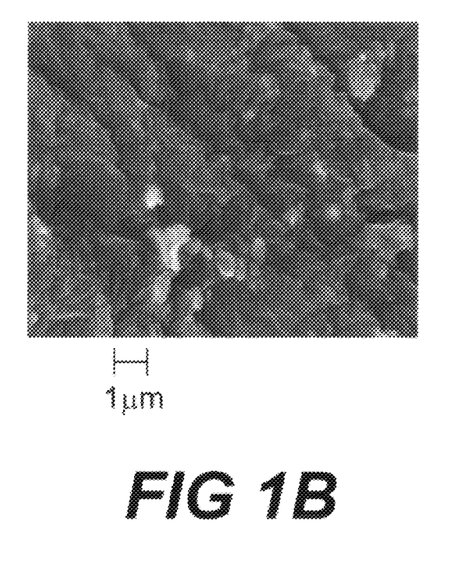

Intermittent fenestrations in the internal elastic lamina, at 0.5-1.5 µm in large vessels and 0.1-0.45 µm in capillaries, allow direct contact between the two cell types, SMCs and ECs. The permeable membrane, according to an exemplary embodiment of the present invention allows bio-macromolecules to pass through, proteins, for example. Exemplary synthesis of the exemplary membrane includes using PEGDM as a porogen mixed with pre-POC polymer solution. After solvent evaporation and post-polymerization, the PEGDM was leached out to obtain a POC' film featured with a couple of sub-micron (nano) surface roughness and with tortuous tunnels inside which are at the same order of fenestration size of elastic lamina. FIGS. 1A and 1B shows SEM images of a POC' membrane in accordance with an exemplary embodiment of the present invention. FIG. 1A shows surface morphology of the membrane, where the scale bar equals 300 nm and FIG. 1B shows the membrane cross-section, where the scale bar equals 1 µm.

Bovine serum albumin (BSA) release experiments indicate that BSA loaded permeable elastic POC' membrane could maintain significant BSA release even at the fourth day while regular POC membrane stopped release in one day. Results support that BSA could penetrate into the tortuous tunnels of the POC' film, while the same is only adsorbed on the surface of regular POC.

This POC' membrane can physically bond to itself. That is one POC' membrane can bond to another POC' membrane, although it is not sticky. The bonding mechanism is attributed to the sub-micron nano-featured surface roughness. Regular POC is not able to bond to itself.

Figure 2A:
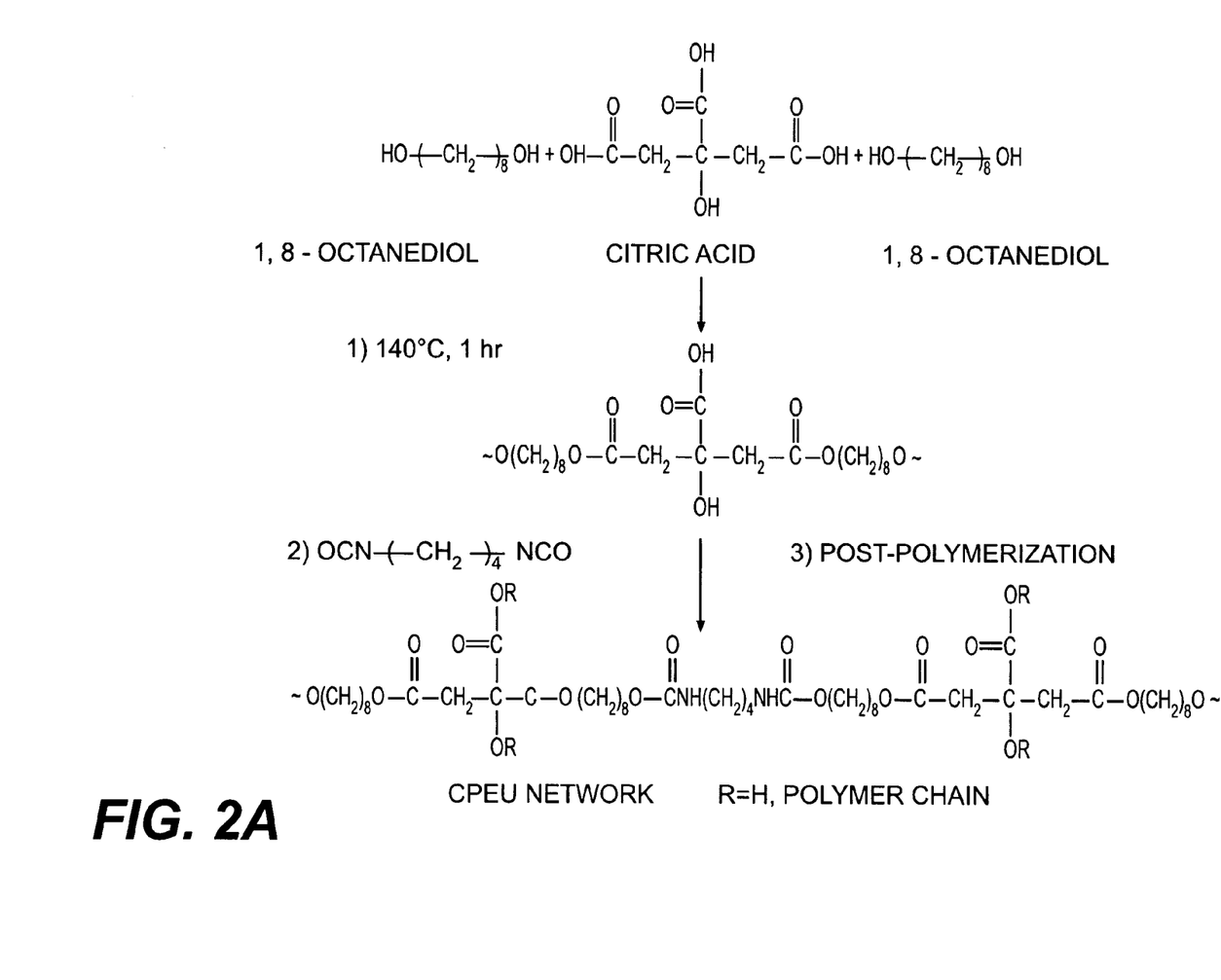
FIGS. 2A-2B show the schematic reaction of an exemplary CUPE synthesis and a schematic of an exemplary CUPE network, respectively.

The synthesis of CUPE comprises at least two distinct steps, as shown in FIG. 2A. In a first step, citric acid and 1,8 octane diol, for example, were added in a molar ratio of 1:1.1 to a 250 ml three necked round bottom flask, fitted with an inlet adapter and an outlet adapter. The mixture was melted within 20 minutes by placing and stirring the contents in the flask in a silicon oil bath maintained at a temperature of 160-165° C. Once the constituents melted, the temperature of the oil bath was reduced to 140° C. and the reaction was allowed to progress for another 75 minutes to create the pre-polymer. This pre-polymer was dissolved in dioxane and then precipitated in water in order to remove any unreacted monomers and oligomers. Following precipitation, the polymer solution was then freeze dried. FIG. 2A shows the schematic reaction of CUPE synthesis.

In a second step, also shown in FIG. 2A, the freeze dried pure polymer was dissolved in N,N'-dimethylformamide (DMF). The urethane linkage is then introduced in this pre-polymer solution by adding 1,6-hexane diisocyanate (HDI) in a 1:0.9, prepolymer to HDI ratio, under continuous stirring to form pre-CUPE.

The time of complete reaction was assessed by Fourier Transform Infra Red Spectroscopy (FT-IR). Some amount of the solution was taken out periodically at 1, 2, 3, and 4 day time points and analyzed by Fourier Transform Infra Red Spectroscopy (FT-IR). The absence of any isocyanate group in the analysis signaled the time point at which the reaction was complete. Pre-CUPE solution was then purified by dropping the solution into water while stirring.

After drying the purified pre-CUPE under vacuum, the CUPE polymers were obtained by heating pre-CUPE at a temperature range from 60-120° C. for times ranging from one day to 2 weeks with or without vacuum in an oven.

According to one exemplary embodiment, an anti-coagulant is incorporated into the CUPE. The ability to incorporate an anti-coagulant into a scaffold for tissue engineered SDBVs may improve the success of the SDBV in vivo. Sodium citrate, the salt form of citric acid, is an anti-coagulant used clinically. In turn, using citric acid as one of the major building blocks for CUPE, is expected to yield a biomaterial with good hemocompatibility.

At least the following monomers can be used to react with citric acid for CUPE synthesis: 1,4-butanediol, 1,6-hexanediol, 1,8-octanediol, 1,10-decanediol, 1,12-dodecanediol. In additional to 1,6-hexamethyl diisocyanate. Any other diisocyanate, such as 1,4-butyl diisocyanate, can be used to synthesize CUPEs.

Ester bonds and urethane bonds present in the CUPE polymer network are degradable. In one exemplary embodiment, 1,4-butyl diisocyanate is used because of its potential for exceptional biocompatibility. One of the degradation products of CUPE, during break-down of urethane bonds, will be putrescine which is already present in the body. Putrescine is believed to play a role in cell growth and differentiation.

In accordance with the present invention, by varying the selection of diols, combination of diols, diisocyanate, and postpolymerization conditions, different CUPE biopolymers may be created.

The multifunctional monomer citric acid is one of the major monomers which can be used to create pre-polymers for CUPE synthesis. Other multifunctional monomers such as malic acid can also be used to create pre-polymers through polycondensation reaction. Multifunctional monomers can be reacted with di-functional monomers, diols to create the pre-polymers. Exemplary aliphatic diols include any diols of between about 2 carbons and about 20 carbons. The diols may be aliphatic, linear, unsaturated diols, with the hydroxyl moiety being present at the C1 and Cx position (where x is the terminal carbon of the diol). The diols may be an unsaturated diol in which the aliphatic chain contains one or more double bonds. Diols can also be macrodiols such poly(ethylene glycol) (PEG) with various molecular weight. Diols can also be a combination of any type of above diols to synthesize the pre-polymers with multifunctional monomers. Amino acids can also be incorporated into the pre-polymers through condensation reactions, for example L-cysteine. Any diisocyanate can be used as linker to bridge pre-polymer chains. For biomedical applications, the diisocyanate used as linker to bridge pre-polymer chains may be any of diphenylsulfone di-isocyanate (SDI), hexamethylene di-isocyanate (HDI) and lysine di-isocyanate (LDI), for example.

CUPE films can be prepared by casting pre-CUPE solution into a Teflon mold followed by solvent evaporation and then post-polymerization under the conditions described as above. Fourier Transform Infra Red Spectroscopy (FT-IR): FT-IR spectroscopy measurements were recorded at room temperature for both CUPE and pre-CUPE. Pre-CUPE FTIR samples were created by casting pre-CUPE solution onto a KBr pellet followed by solvent evaporation to form thin films. CUPE FTIR samples were created by post-polymerizing the pre-CUPE thin films on the KBr pellet. FTIR spectroscopy measurements were recorded at room temperature for both CUPE and pre-CUPE. CUPE in the following exemplary embodiments are made with citric acid, 1,8-octanediol, and HDI except where specified otherwise.

Differential Scanning Calorimetry (DSC) was performed on a DSC550(Instrument Specialists Inc. Spring Grove, Ill.) to study the thermal behavior of the new polymers. Samples are first scanned up to 150° C. with a heating rate of 10° C./min under nitrogen purge (50 ml/min). A hole was drilled in the aluminum crucible.

Two cycles of cooling were performed. The first round of heating can help to get rid of the trace of water from sample. Thereafter cooled with a cooling rate of −40° C./min to −60° C. and recorded a second time up to 230° C. The glass transition temperature (Tg) is determined as the middle of the recorded step change in heat capacity from the second heating run.

In accordance with an embodiment of the present invention, tubular scaffolds of a CUPE polymer were fabricated using tubular Teflon moulds using a method previously described by Yang et al. (Yang et al., Biomaterials, 2006, 11(11-12): pp. 1876-1886). The CUPE pre-polymer was dissolved in 1,4-dimethylformamide, to form a 30% solution. Sieved salt (106-150 microns) was added in a 1:6, prepolymer: salt weight ratio to form a slurry, which was cast into the tubular Teflon mould and allowed to dry for 24 hours. After solvent evaporation, the moulds were put into an oven maintained at 80° C. for a period of two days for post polymerization under mild conditions. Subsequently, another day of postpolymerization at high temperature and vacuum (120°

C., 0.01 inches of Mercury, respectively) is done. The salt was removed by leaching in de-ionized water (produced by a Millipore water purification system, Millipore, Billerica, Mass.) for a period of 72 hours with water changes every 3 hours. The tubular scaffolds obtained after leaching were lyophilized for 48 hours to remove all traces of water.

Figure 3A:
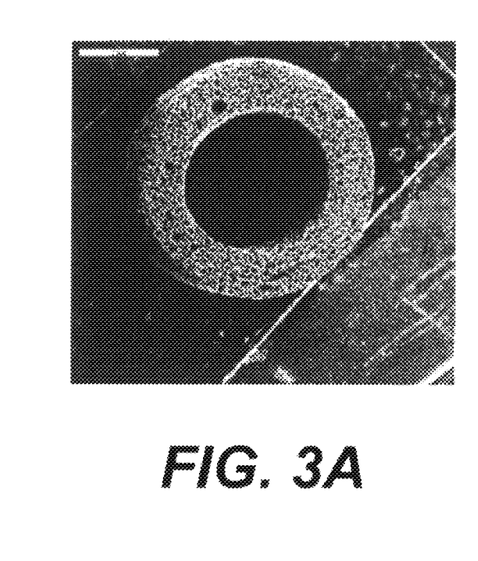
FIGS. 3A-3C show an SEM picture of a cross section of a tubular scaffold diameter at different magnifications according to an exemplary embodiment of the present invention.
Figure 3B:
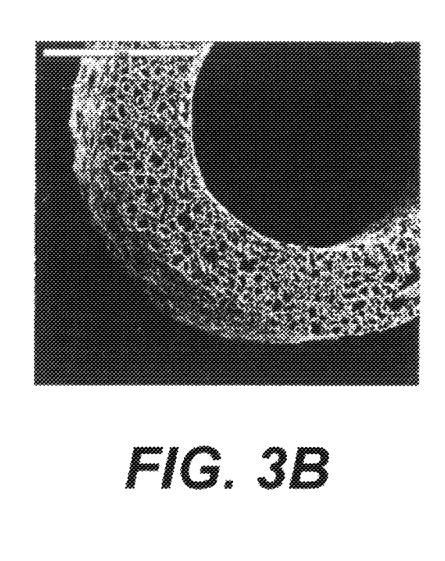
Figure 3C:
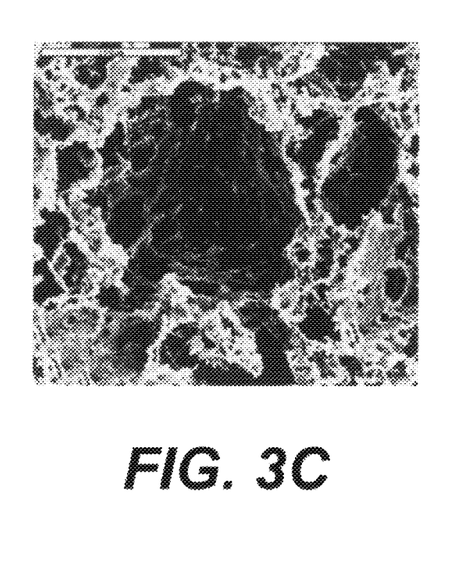

The tubular scaffolds obtained were examined qualitatively for elasticity and strength and by SEM observation. Scaffold were freeze fractured using liquid nitrogen and then cross-sectioned. The cross section of the fractured tubes was examined under SEM. FIGS. 3A-3C show a SEM picture of a cross section of a tubular scaffold diameter at different magnifications according to an exemplary embodiment of the present invention.

Cell seeding can be done on the CUPE polymer films in accordance with the present invention. For example, polymer films, in accordance with the present invention, were formed by casting pre-CUPE solutions in glass vials which could be placed in a 24 well plate. The 24-well plate was divided into 12 wells for the CUPEs and another 12 wells for regular POC, which acted as the control. Three ml of a 30% polymer solution was cast into each vial and allowed to air dry for 24 hours. After drying, the glass vials were allowed to polymerize under mild conditions, in an oven maintained at 80° C. for two days, following which they were post polymerized to introduce further crosslinking, by heating at 120° C. under high pressure (0.01 inches of mercury). The polymer films were sterilized by addition of 70% ethanol. After 30 minutes, the ethanol was removed by exchanging with an excess amount of phosphate-buffered saline (PBS). Ethanol treatment was followed by exposure to ultra-violet (UV) light for another 30 minutes.

Figure 4A:
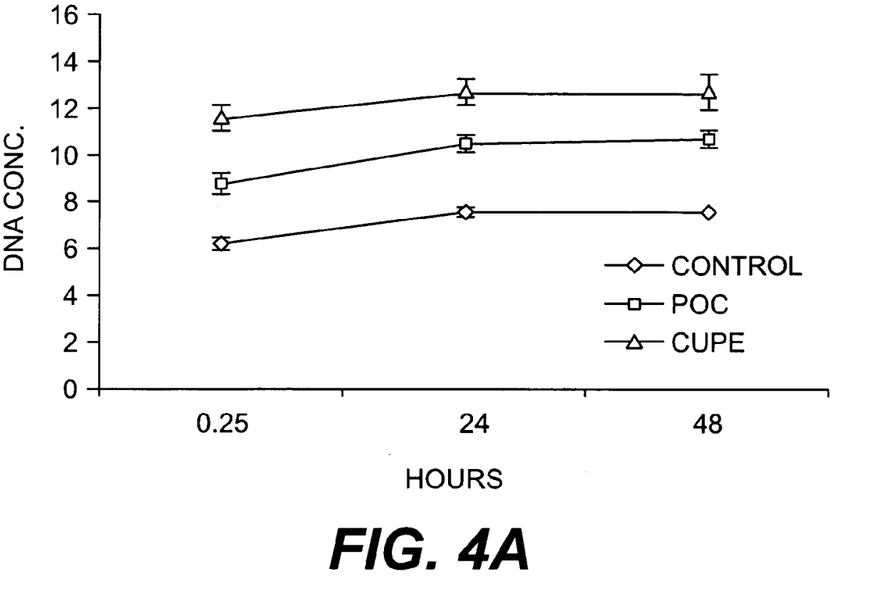
FIGS. 4A and 4B graphically represent the results of cell attachment and proliferation assays, respectively, in accordance with an exemplary embodiment of the present invention.
Figure 4B:
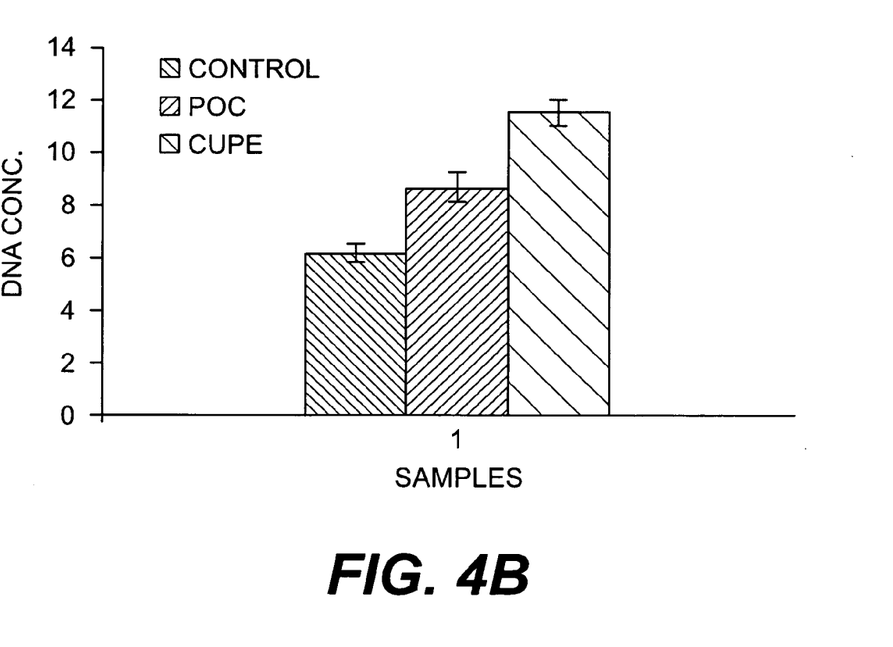

Two ml of cell suspension containing $3\times10^3$ cells human aortic endothelial cells (HAECs) were added to each of the 24 wells and the 12 glass vials. An attachment assay was conducted after 6 hours using the Pico-Green DNA Assay. The proliferation of the cells on the polymers and the glass was studied one day and three days after seeding the cells on the vials, using the Pico-Green DNA assay. FIGS. 4A and 4B show exemplary results of cell attachment and proliferation assays, respectively, in accordance with an exemplary embodiment of the present invention. FIGS. 4A and 4B are graphs depicting the results of the cell attachment assay (A) and cell proliferation assay (B). Attachment assay was done 6 hours after cell seeding. Proliferation assays were done on Day 1 and Day 2 after seeding. Control-Glass, P1-POC and P2-CUPE polymer film, respectively.

Figure 5A:
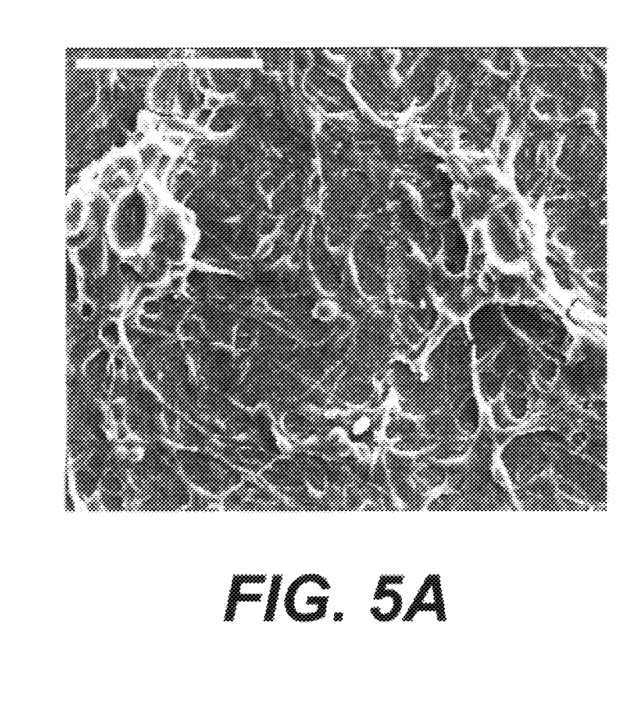
FIGS. 5A and 5B show SEM images of a CUPE polymer, where A) depicts the morphology of fibroblasts seeded and adhered to a CUPE polymer in accordance with an exemplary embodiment of the present invention and B) depicts a CUPE polymer film without any cell seeding.
Figure 5B:
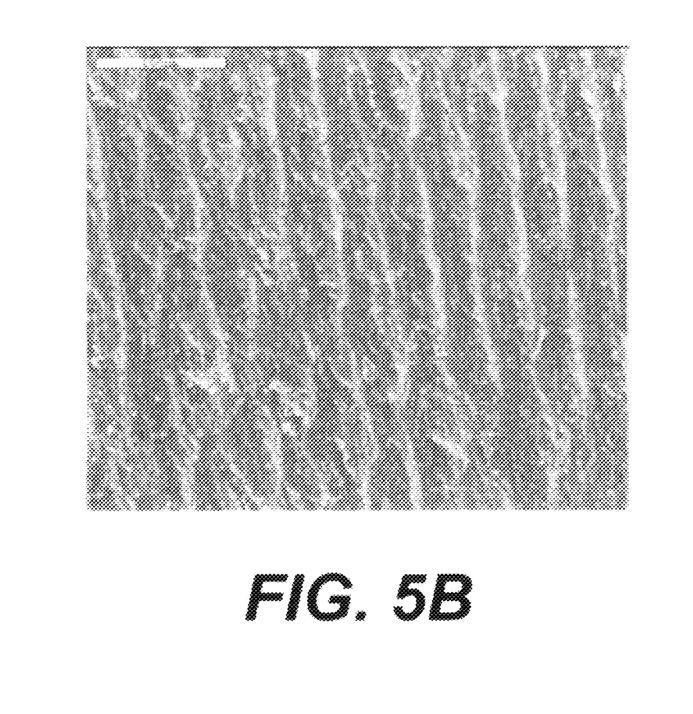

CUPE polymer films were cut into small pieces ($1\times2$ cm$^2$) and placed in cell culture-petri-dishes (diameter 6 cm). Sterilization was carried out by the aforementioned process. A 5 ml cell suspension with $6\times10^4$ cells (NIH 3T3 fibroblasts) was added to the film on the culture dish, which was further supplemented with 10 ml of media. Cells were allowed to grow on the surface of the film for two days, after which the films were transferred to a fresh culture dish with the same volume of media. The culture was allowed to go on for a pre-determined time period. After reaching confluence, the polymer samples seeded with cells were fixed by addition of 2.5% glutaraldehyde solution and incubation for 2 hours. Then the films were sequentially dehydrated in 50%, 75%, 95% and 100% ethanol, each for 10 minutes. The samples were lyophilized, sputter coated with copper and examined under a SEM (JEOL 845, Peabody, Mass., U.S.A). SEM pictures were taken to study the morphology of the cells growing on the surface of the polymer. FIGS. 5A and 5B show 3T3 fibroblast morphology via SEM on seeded CUPE film and non-seeded blank CUPE film, respectively.

Figure 6A:
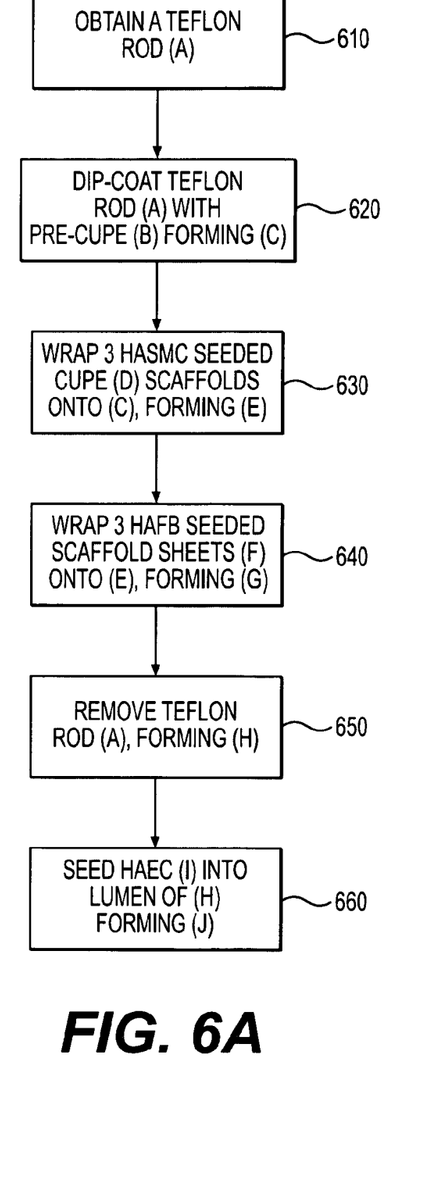
FIGS. 6A and 6B show a flowchart and a schematic of vascular graft fabrication, respectively, tissue engineering, by cell sheet design, in accordance with an exemplary embodiment of the present invention.
Figure 6B:
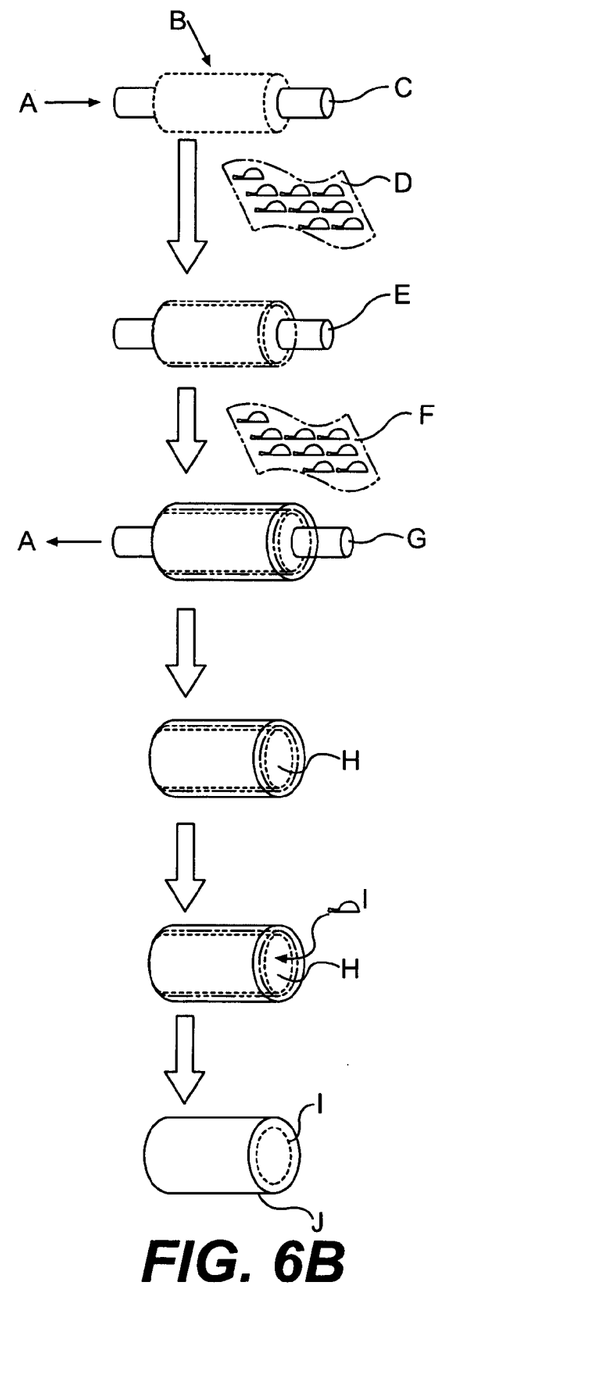

FIGS. 6A and 6B show a flowchart and a schematic of vascular graft fabrication, respectively, in accordance with an exemplary embodiment of the present invention. Tissue engineering of vascular grafts, using a scaffold-sheet design, in accordance with the present invention, begins with a CUPE tubular scaffold (A) and CUPE sheets (D, F), as shown for example in FIG. 6B. A CUPE tube (B) may be dip coated about a Teflon Rod (A). Exemplary dimensions are a 3 mm diameter Teflon rod and a 100 µm thick CUPE tube. Human aortic fibroblasts (HAFBs), human aortic smooth muscle cells (HASMCs), and HAECs (Clonetics, Walkersville, Md.) may be cultured in a 50 ml flask with FGM-2, SmGM-2, and EBM-2 culture medium, respectively. Cell culture may be maintained in a water-jacketed incubator equilibrated with 5% $CO_2$ at 37° C. Cells may be limited to fifth passage cells.

CUPE may be used to fabricate a vascular graft using a cell sheet engineering technique. This may be done in a two step process. In step one, the porous polymer scaffolds and nanoporous polymer tubes are fabricated. Briefly, the purified or non-purified CUPE pre-polymer solution in DMF or Dioxane, for example a 10% pre-CUPE solution, may be cast on a stainless steel plate with dimension 5 cm (l)×5 cm (w)×150 µm (d) to obtain a 150 µm thick liquid membrane on the plate. The solution may be cast on a stainless steel plate with dimensions 5 cm (l)×5 cm (w)×150 µm (d), to obtain a 150 µm thick membrane on the plate.

The above liquid membrane may be freeze-dried to remove all traces of solvent and then subjected to post-polymerization in an oven at 80° C. for 2 weeks to obtain macroporous CUPE scaffolds. Post-polymerization time can vary. CUPE polymer tubes can be produced by dip-coating a Teflon rod with pre-CUPE/PEGDM. PEGDM (Mw=250, 20 wt % of pre-CUPE) acts as a porogen to create nano-features, such as nano-scale tortuous tunnels, on the CUPE tubes. After solvent evaporation, the pre-CUPE/PEGDM coated Teflon rod can be transferred into an oven for post-polymerization and then followed by PEGDM leaching and freeze-drying to obtain nano-featured, nanoporous, CUPE tubes.

According to the exemplary embodiment shown in FIG. 6B and described in the fabrication flowchart of FIG. 6A, multiple CUPE scaffold sheets and a CUPE tube will be used for cell seeding and fabricating a vascular graft. Referring to FIGS. 6A and 6B, a nano-featured CUPE tube (B) may be made as described above. A CUPE tube (B) is fabricated by dip coating using a Teflon rod (A), forming (C) 620. Three HASMC seeded CUPE scaffold sheets (D) are wrapped around (C), forming (E) 630. Three HAFB seeded CUPE scaffold sheets (F) are wrapped around (E), forming (G) 640. The Teflon rod (A) is removed, forming (H) 650. HAECs (I) are seeded in the lumen of (H) forming (J) 660, which is a vascular graft complete with an endothelial lined lumen.

More particularly, scaffold sheets 1, 2 and 3 may be seeded with HAFBs by pipetting $5\times10^6$ cells/ml of human aortic fibroblasts (HAFBs) evenly into the scaffold; Scaffold sheets 4, 5 and 6 may be seeded with human aortic smooth muscle cells (HASMCs) by pitpetting $5\times10^6$ cells/ml of HASMCs evenly into the scaffold; After two days of in vitro culture, A CUPE tubular graft will be constructed by rolling HASMCs seeded CUPE sheets and HAFBs seeded CUPE sheets on the CUPE tube sequentially with the aid of a Teflon rod (3 mm in diameter) inserted in the CUPE tube. Then human aortic endothelial cells (HAECs) with a density of $1\times10^6$ cells/ml will be seeded on the lumen of the tubular graft according a method described previously. (Yang et al., Adv Mater, 2006. 18(12): p. 1493-149851). The resulting cell-seeded CUPE graft (about 1 mm thick wall) will be further cultured in vitro for three days for further bonding between the layers of the graft. (Williams et al., Annals of Biomedical Engineering, 2005. 33(7): p. 920-928). The number of respective CUPE scaffold sheets and thickness of the CUPE tube can vary as needed.

Crosslinked urethane polyester elastomers (CUPEs) eliminate the disadvantages, and combine the advantages of both polyurethanes and crosslinked polyesters. Hence, CUPEs are candidates for tissue engineering scaffolds to include small diameter vascular grafts. This new family of CUPE elastomers, according to the present invention, are an improvement over the previously reported poly(diol citrate) family. Poly(diol citrates) are utilized as a base material for CUPE synthesis.

Figure 2B:
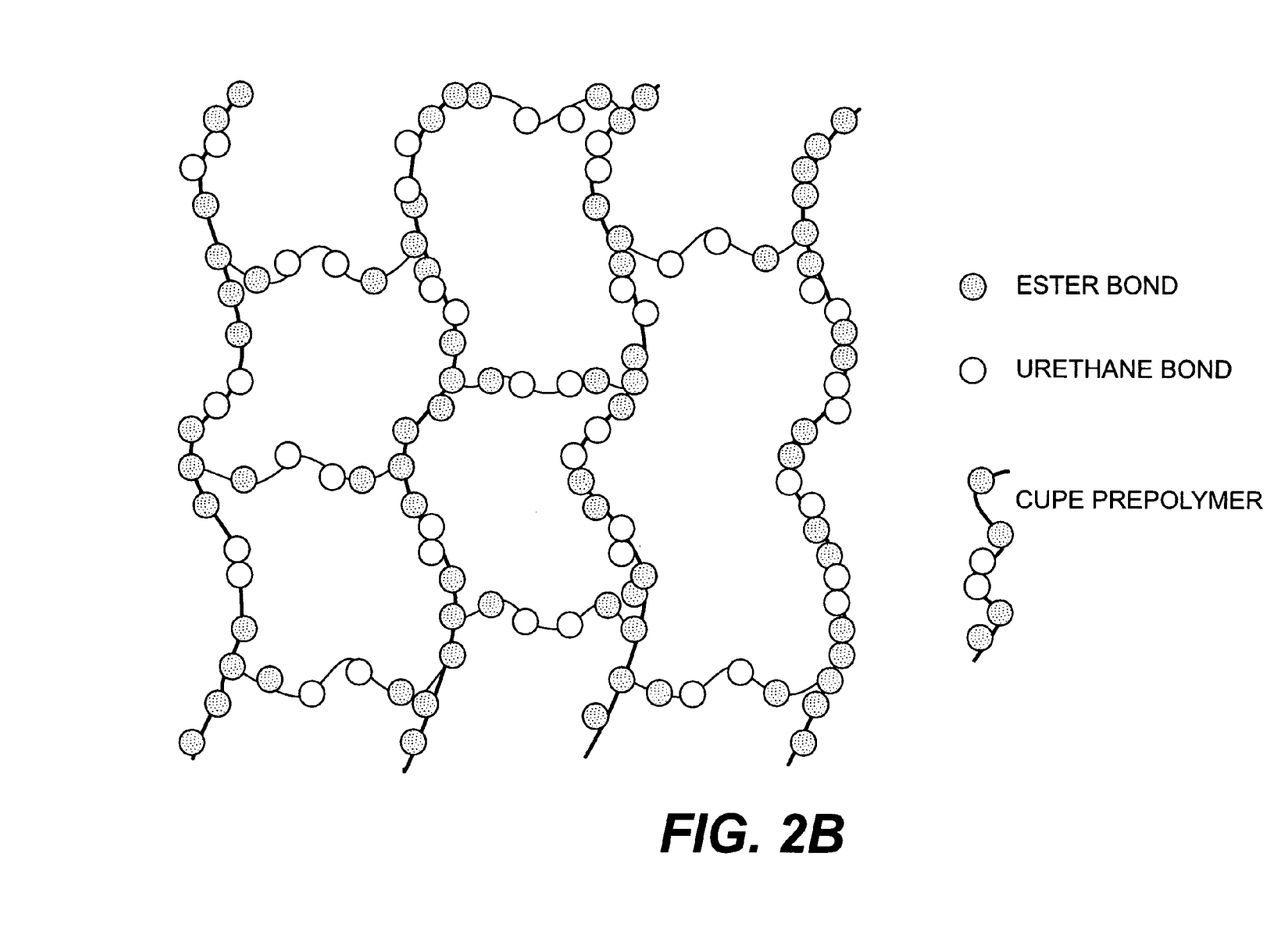

In the case of using citric acid, 1,8-octanediol, and 1,6-hexamethyl diisocyanate (HDI), pre-Poly(1,8-octanediol citrates) (pre-POC) are first synthesized by the polycondensation of citric acid and 1,8-octanediol, to result in a pre-polymer which is used for the synthesis of the CUPE. A 1/1.1 molar ratio of citric acid/1,8-octanediol is used for this synthesis, so as to cap the two ends of the polymer chains with hydroxyl groups. In order to synthesize CUPE, small quantities of HDI are added to the pre-polymer solution and the reaction is continued till all the diisocyanate is used up. The diisocyanate will react with the end hydroxyl groups of the POC polymer chains to form the urethane linkages. The urethane linkages act as bridges between the POC polymer chains which link together to form a polymer (pre-CUPE) which has a higher molecular weight compared to the linear pre-POC as depicted in the FIG. 2. Pre-CUPE can be further crosslinked by heating firstly under mild conditions of 80° C. for two days, followed by 120° C. under vacuum or one day, to form CUPE polymers.

Figure 7A:
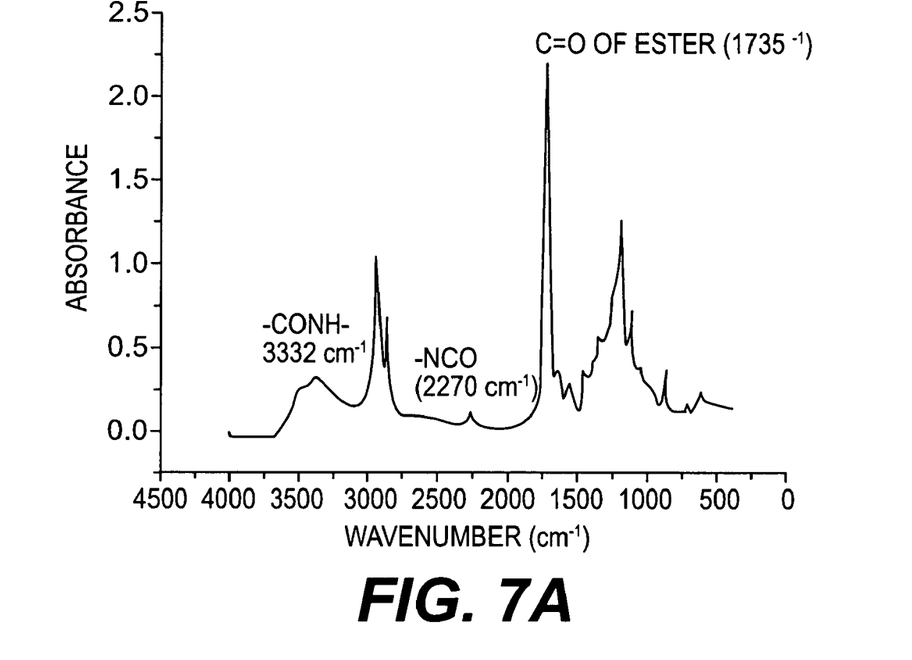
FIGS. 7A and 7B show an FT-IR spectrum of CUPE with pre-polymer-isocyanate in a 1:0.6 molar ratio, according to an exemplary embodiment of the present invention, and thermogram results of an exemplary embodiment of the present invention, respectively.
Figure 7B:
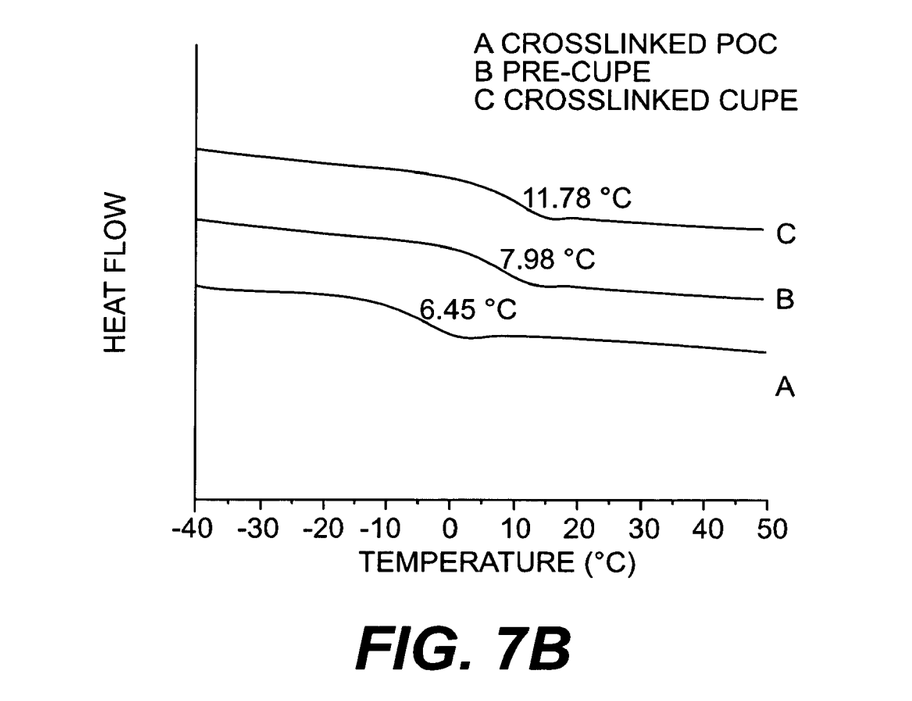

The typical FT-IR spectrum of pre-CUPE is shown FIG. 7. The presence of ester bonds is denoted by the intense C=O stretch at 1,735 $cm^{-1}$ and the intense peak at 3332 $cm^{-1}$ indicates the formation of the urethane bonds. Note the absence of a peak at 2,267 $cm^{-1}$ indicating that all the diisocyanate has reacted completely.

Thermal properties of the CUPEs were investigated using differential scanning calorimetry (DSC). For the thermograms, shown in FIG. 7B, POC is crosslinked during post-polymerization at 80° C. for one day A. CUPE is also crosslinked during during post-polymerization at 80° C. for one day C. And pre-CUPE, shown as B, has not been subject to any crosslinking. From FIG. 7, it can be seen that the glass transition temperature of the pre-CUPE (B) which has not been subjected to any crosslinking is higher than that of the crosslinked POC (A) control. The higher molecular weight and hydrogen bonding of urethane bonds of the CUPE could be responsible for this phenomenon. The CUPE's ability to crosslink is also demonstrated in the figure. The higher glass transition temperature of the crosslinked CUPE (C) compared to the un-crosslinked CUPE (B) indicates that the polymer chains have been crosslinked and a greater amount of heat must be supplied to make the polymer chains flow. Another indication of crosslinking is that pre-CUPE can be dissolved in solvent such as 1,4-dioxane, Dimethyl sulfoxide (DMSO), and N,N-Dimethylformamide (DMF) while CUPE is not soluble in any solvent.

This new family of CUPE polymers was assessed for biocompatibility with respect to cell adhesion and cell growth. NIH 3T3 fibroblasts and human aortic endothelial cells were used as model cells for this study. The 3T3 fibroblasts were seeded and allowed to grow on a small CUPE film for a total of two days and then imaged using high resolution SEM. FIG. 5A shows the morphology of the confluent cells on the surface of the seeded polymer films. From the SEM images, it can be seen that the cells spread out over the surface with extended filopodia, which were in contact with other cells. This indicates that the cells maintained a healthy morphology while they grew on the polymers, which meant that the CUPE polymer films are conducive to cell adhesion and growth.

The attachment and proliferation assays showed that the human aortic endothelial cells showed a good affinity for the CUPE polymers. The results of the attachment and proliferation assays are depicted in FIG. 4A and 4B, respectively. It was observed that the cells attached to the CUPE in much greater numbers compared to the control glass and POC films. In addition to the initial attachment, the cells showed a greater tendency to grow and proliferate on the CUPE polymer films in comparison to glass and regular POC.

The graphs of FIGS. 4A and 4B depict the results of the cell attachment assay (A) and cell proliferation assay (B). The attachment assay was done 6 hours after cell seeding. Proliferation assays were done on Day 1 and Day 2 after seeding. Glass was the control (Control) and regular POC is designated (P1), while CUPE polymer film in accordance with an exemplary embodiment of the present invention is (P2).

Figure 8A:
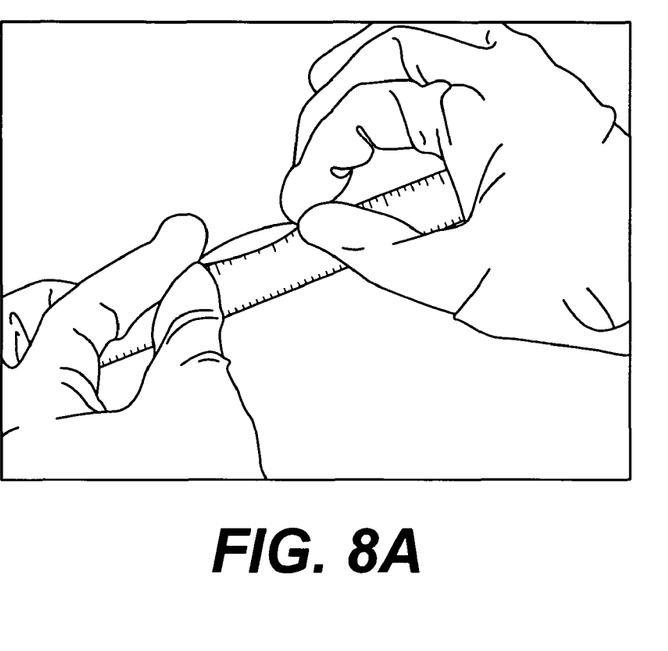
FIGS. 8A and 8B show photographs of a porous CUPE scaffold before stretching (A) and after stretching with near 220% elongation (B)
Figure 8B:
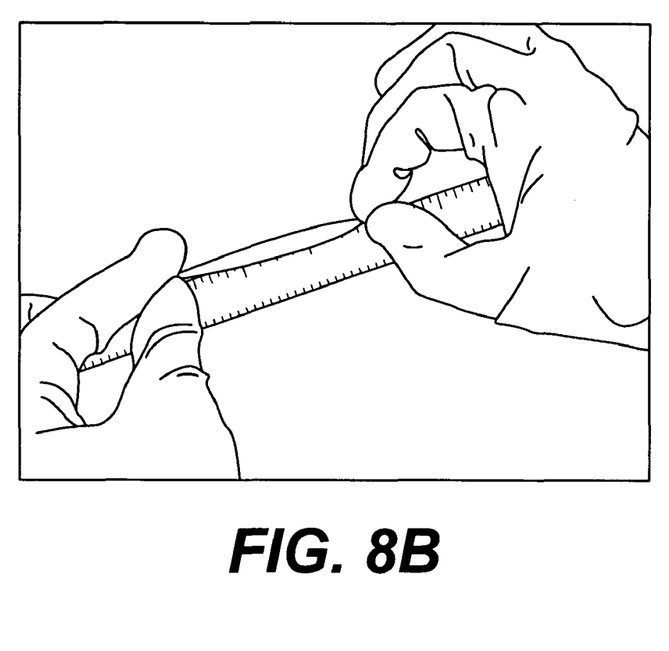

The tubular scaffolds fabricated using the CUPE polymer were evaluated for elasticity and compared that of regular POC tubular scaffolds. CUPE tubular scaffolds had greater elasticity and mechanical strength compared to the regular POC tubular scaffolds. The CUPE tubular scaffolds showed an elongation of 220% without break, as shown in FIGS. 8A and 8B. This is a significant achievement over the mechanical and elastic properties of the POC scaffolds which only showed a 70% of elongation before rupturing.

Figure 9:
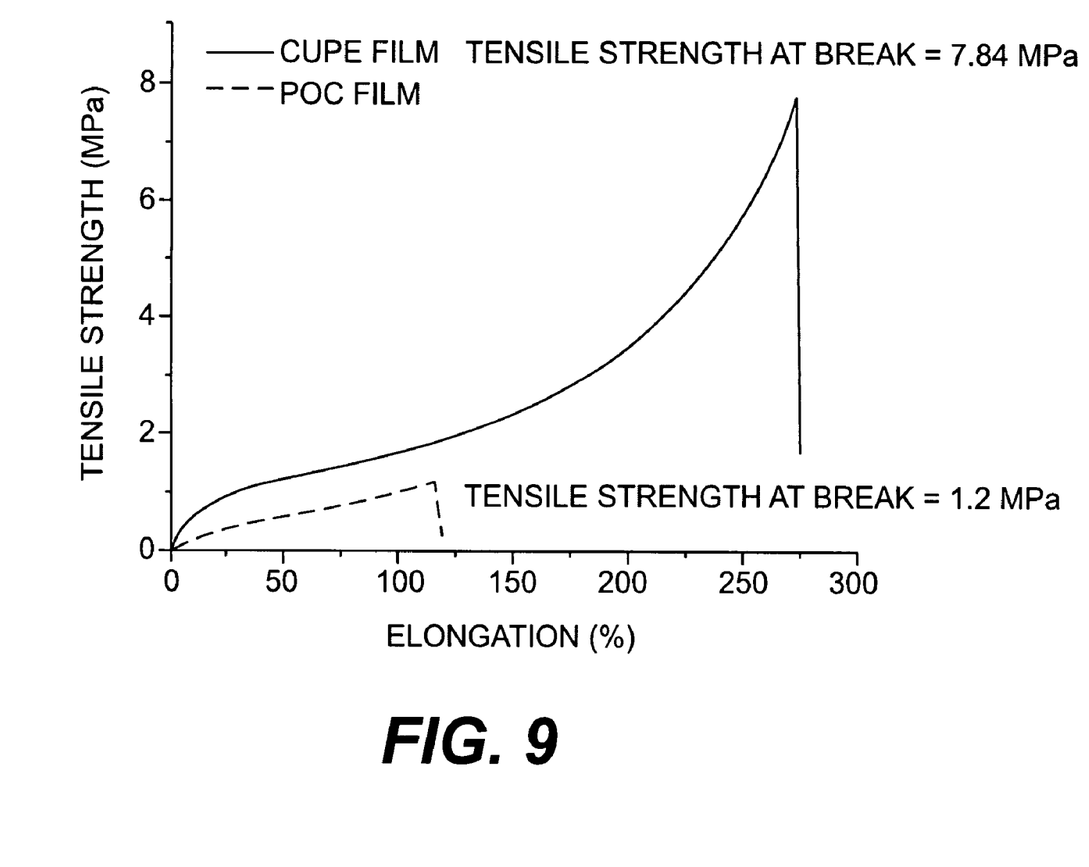
FIG. 9 shows the results of a tensile strength test on an exemplary embodiment of the present invention.

FIG. 9 is a graph of mechanical tests for CUPE films and POC films synthesized under the same conditions. CUPE films and POC films were synthesized by post-polymerizing pre-CUPE and pre-POC at 80° C. for two days and then at 120° C., 2 Pa, for one day. Tensile mechanical tests for CUPE were conducted on a MTS Insight II mechanical tester. CUPE films were cut into dog-bone-shape samples according to ASTM D412. A 500 N load cell was used at a crosshead speed of 500 mm/min. The mechanical data shown graphically in FIG. 9 supports that introducing urethane bones into the polyester network can greatly increase the tensile mechanical strength and elongation of the polymers. CUPE yielded a 7.84 MPa breaking strength and a 280% elongation, while control POC yielded a 1.2 MPa breaking strength and an elongation of 125%. This result supports that the new CUPE can combine the advantages of strong polyurethane and soft and elastic poly(diol citrates).

SEM images of the tubular scaffold cross section, FIGS. 3A-3C showed the formation of an interconnected highly porous network, which is expected to be beneficial to the cell growth and interaction. FIG. 3A, shows the thickness of the tube is observed to be uniform (Scale Bar 2 mm). The SEM picture of the cross section showing the pores on the cross section (Scale Bar 2 mm), FIG. 3B. And SEM picture of a single pore on the scaffold cross section shows interconnected pores (Scale Bar 200 microns), FIG. 3C.

This invention described herein creates a family of crosslinked urethane-containing polyester (CUPE) for biomedical applications, and particularly soft tissue engineering. The synthesis of CUPE is simple, safe, and cost-effective. CUPEs hold great potential for tissue engineering owing to their controlled degradability, mechanical properties, and excellent biocompatibility. In combination with the layer-by-layer scaffold sheet engineering technique, these materials may be fashioned into small diameter vascular grafts or any other tissue implants with the requisite strength and elasticity to be implanted in the body. The introduction of CUPE should expand the repertoire of available biodegradable polymers to meet the requirements of tissue engineering and other biomedical applications.

The potential applications of this novel family of polymers can be soft tissue engineering, drug delivery and orthopedic devices. Soft tissue engineering applications may include engineering blood vessels, cardiac tissues, heart valves, skin bladder, tendon, ligament, and meniscus.

The high-molecular-weight pre-CUPEs and CUPEs can all be used as biomaterials for biomedical applications. The layer-by-layer scaffold sheet engineering design can be used to fabricate any tissue grafts, especially for small diameter blood vessel and cardiac tissue grafts. CUPE can potentially be used for any tissue engineering applications, in particularly soft tissue engineering, such as blood vessels, cardiac tissues, ligaments, tendons, cartilage, bladders, skins, trachea, urethral etc. CUPE can also be used to prepare composite materials with other polymers or inorganic materials or combination of them. One example is CUPE can be hybrid with inorganic hydroxyapatite (HA) to prepare bone implants. Degradation rates and mechanical properties of CUPEs can be controlled by varying the types and combinations of the monomers, and the synthesis conditions. Applications for the bio-polymer described herein include, for example, blood vessels.

CUPE can be used to prepare micro-spheres or nano-spheres for drug delivery applications. CUPE can be fabricated into scaffolds via any method, such as, salt-leaching, freeze-drying, or 3-D printing. CUPE can be spun into micro- or nano-fibers. The fiber scaffolds can act as extracellular matrix (ECM) for biomedical applications. The biodegradable fibers can be used in any woven or nonwoven applications. The available functional groups on CUPE include hydroxyl and carboxyl groups. These groups can be further used for surface modification or functionalization.

While specific alternatives to steps and elements of composition of the invention have been described herein, additional alternatives not specifically disclosed but known in the art are intended to fall within the scope of the invention. Thus, it is understood that other ions of the present invention will be apparent to those skilled in the art upon reading the described embodiment and after consideration of the appended claims and drawing.

What is claimed is:

1. A method of synthesizing a biomaterial cross-linked urethane-doped polyester polymer comprising the steps of:
    combining at least one multi-functional monomer comprising at least 2 carboxyl and at least one diol to form a polyester polymer;
    adding one or more di-isocyanate monomers to the polyester polymer to form a urethane doped polyester; and
    forming ester-bond crosslinks between the urethane doped polyester through the condensation of the side carboxyl groups and hydroxyl groups on the polyester polymer chains to form a crosslinked urethane doped polyester polymer network with one or more urethane/urea bonds doped in the polyester chains between the ester-bond crosslinks.

2. The method of claim 1, further comprising the step of adding di-isocyanate monomer to the polyester polymer and extending the polyester polymer by adding diamine or diol monomers or their combinations to the polyester polymer to form an extended urethane doped polyester which can be further crosslinked by ester bond formation to form crosslinked urethane doped polyester network.

3. The method of claim 1, further comprising: mixing a porogen in with the urethane doped polyester to create nano-featured scaffolds.

4. The method of claim 3, wherein the porogen is poly (ethylene glycol)dimethyl ether.

5. The method of claim 3, wherein the at least one multi-functional monomer comprises citric acid.

6. The method of claim 1, wherein L-cysteine is incorporated into the pre-polymer.

7. A method of synthesizing a biomaterial polymer, the method comprising:
    forming pre-polymers via polycondensation of multifunctional monomers and diols;
    adding a diisocyanate as a linker of the pre-polymers to introduce urethane bonds into the formed pre-polymers to form urethane-containing linear polymers;
    crosslinking the urethane-containing linear polymers through forming ester-bond crosslinks via condensation reactions between the side carboxyl groups and the hydroxyl groups in the linear polymers to form crosslinked urethane-containing (doped) polyester network.

8. The method of claim 7, wherein the diisocyanate used as linker to bridge pre-polymer chains is selected from a group consisting of diphenylsulfone di-isocyanate (SDI), hexamethylene di-isocyanate (HDI) and lysine di-isocyanate (LDI).

9. The method of claim 7, wherein at least one of citric acid and malic acid is a multifunctional monomer used in the forming of the crosslinked polymer via polycondensation.

10. The method of claim 7, wherein multifunctional include diols, to create the pre-polymers.

11. The method of claim 10, wherein the diols are aliphatic diols, which comprise between 2 and 20 carbons, inclusively.

12. The method of claim 10, wherein the diols are aliphatic, linear, unsaturated diols, with a hydroxyl moiety being present at the C1 and Cx position, wherein x is the terminal carbon of the diols.

13. The method of claim 10, wherein the diols are unsaturated, in which an aliphatic chain contains one or more double bonds.

14. The method of claim 10, wherein the diols are macrodiols and may have various molecular weights.

15. The method of claim 14, wherein the macrodiols are poly(ethylene glycol) (PEG).

16. The method of claim 10, wherein a combination diols react with multifunctional monomers to synthesize the pre-polymers.

17. The method of claim 7, further comprising incorporating amino acids into the pre-polymers through condensation reactions.

18. The method of claim 17, wherein L-cysteine is the amino acid incorporated into the pre-polymer.

19. A method of synthesizing a biomaterial cross-linked urethane-containing polyester polymer-comprising the steps of:
    combining at least one multi-functional acid containing monomer and at least one diol to form a polyester polymer;
    adding one or more di-isocyanate monomers to the polyester polymer to form a urethane doped polyester;
    forming ester-bond crosslinks between the urethane doped polyesters by the condensation of side carboxyl groups and hydroxyl groups on the urethane doped polyester to form a crosslinked urethane doped polyester polymer network; and
    adding one or more porogens to the crosslinked urethane doped polyester polymer network;

leaching out at least a portion of the one or more porogens; or adding di-isocyanate monomer to the polyester polymer to form isocyanate terminated polyesters;

adding diamine or diols monomers to extend the urethane doped polyester to form an extended urethane doped polyester polymer; and crosslinking the extended urethane doped polyester via ester-bond crosslinks formed by the condensations of the side carboxyl groups and hydroxyl groups on the extended urethane doped polyester polymers to form crosslinked urethane doped polyester network; or adding more di-isocyanates as crosslinkers to crosslink urethane-doped polyester polymers.

* * * * *